United States Patent [19]

Levin et al.

[11] Patent Number: 5,286,729
[45] Date of Patent: Feb. 15, 1994

[54] ANGIOTENSIN II RECEPTOR BLOCKING 2,3,6 SUBSTITUTED QUINAZOLINONES

[75] Inventors: Jeremy I. Levin, Nanuet; Aranapakam M. Venkatesan, Elmhurst, both of N.Y.

[73] Assignee: American Cyanamid Company, Wayne, N.J.

[21] Appl. No.: 52,935

[22] Filed: Apr. 23, 1993

[51] Int. Cl.$^5$ .............. A61K 31/505; C07D 401/14; C07D 401/12; C07D 405/12
[52] U.S. Cl. .................. 514/259; 544/92; 544/283; 544/284; 544/287
[58] Field of Search ............ 544/284, 283, 287; 514/259

[56] References Cited

U.S. PATENT DOCUMENTS

| | | | |
|---|---|---|---|
| 5,162,325 | 11/1992 | Chakravarty et al. | 544/284 |
| 5,202,322 | 4/1993 | Allen et al. | 544/284 |
| 5,204,354 | 4/1993 | Chakravarty et al. | 544/283 |

FOREIGN PATENT DOCUMENTS

| | | |
|---|---|---|
| 407342 | 1/1991 | European Pat. Off. |
| 411766 | 2/1991 | European Pat. Off. |
| 445811 | 9/1991 | European Pat. Off. |
| 481448 | 4/1992 | European Pat. Off. |
| 512870 | 11/1992 | European Pat. Off. |

*Primary Examiner*—Emily Bernhardt
*Attorney, Agent, or Firm*—Thomas S. Szatkowski

[57] ABSTRACT

The invention provides novel 2,3,6 substituted quinazolinones having the formula

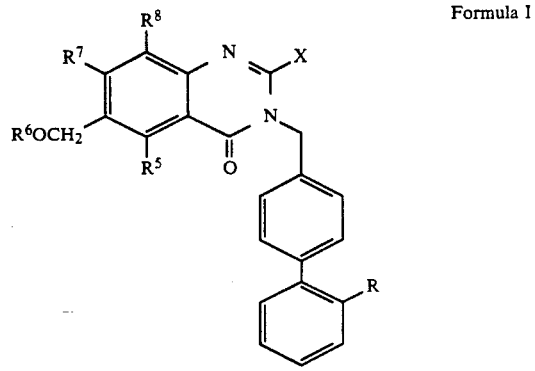

Formula I wherein R, $R^5$, $R^6$, $R^7$, $R^8$ and X are described in the specification which have activity as angiotensin II (AII) antagonists.

19 Claims, No Drawings

ANGIOTENSIN II RECEPTOR BLOCKING 2,3,6 SUBSTITUTED QUINAZOLINONES

BACKGROUND OF THE INVENTION

1. Field of the Invention

This invention relates to certain novel 2, 3, 6 substituted quinazolinone compounds which have demonstrated activity as angiotensin II (AII) antagonists and are therefore useful in alleviating angiotensin induced hypertension and for treating congestive heart failure.

SUMMARY OF THE INVENTION

According to the present invention, there are provided novel compounds of Formula I which ave angiotensin II-antagonizing properties and are useful as antihypertensives:

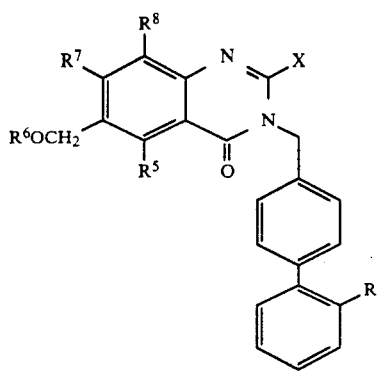

Formula I

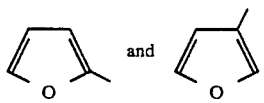

and the pharmaceutically acceptable salts of these compounds.

The present invention also provides novel intermediate compounds, methods for making the novel 2,3,6 substituted quinazolinone angiotensin II antagonizing compounds, methods of using the novel quinazolinone angiotensin II antagonizing compounds to treat hypertension, congestive heart failure and to antagonize the effects of angiotensin II.

DETAILED DESCRIPTION OF THE INVENTION

The novel compounds of the present invention are prepared according to the following reaction schemes.

Referring to Scheme I, the corresponding anthranilic acid 2 where $R^5$, $R^7$ and $R^8$ are defined before and wherein $R^{20}$ is I, Br or $CH_3$, are heated to reflux in alkyl acid anhydride 3 wherein X is alkyl of 3 to 5 carbon atoms to provide the 4H-3,1-benzoxazin-4-ones 4 which are isolated by concentrating the reaction mixtures and used without further purification. When the 4H-3,1-benzoxazin-4-ones 4 are refluxed in ethyl alcohol containing ammonia, or ammonium hydroxide solution, the quinazolinone intermediates 5 are obtained.

Scheme I

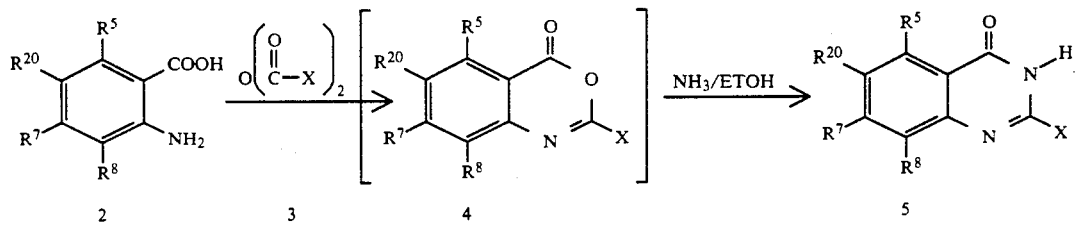

wherein:
R is

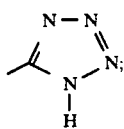

X is straight or branched alkyl of 3 to 5 carbon atoms;
$R^5$, $R^7$ and $R^8$ are H;
$R^6$ is

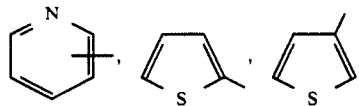

The quinazolinone intermediates 5 are modified according to the following reaction schemes to obtain the novel quinazolinone Angiotensin II antagonist compounds of the present invention.

In Scheme II, 6-methylquinazolinone 6, as prepared by Scheme I, is brominated with N-bromosuccinimide to give the bromomethyl compound 7. Hydrolysis of the bromide with aqueous potassium carbonate in dimethylsulfoxide yields the primary alcohol 8.

Scheme II

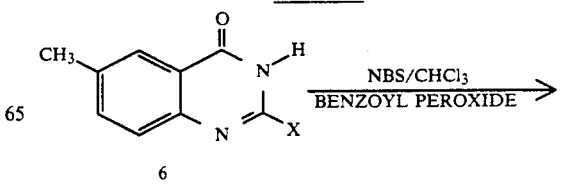

3
-continued
Scheme II

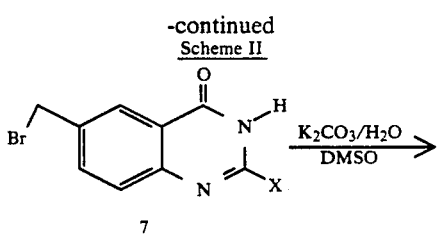

In an alternate route to 8, as shown in scheme III, 2-alkylsubstituted-6-iodo-4(1H)-quinazolinone 9, prepared by Scheme I is reacted via a palladium catalyzed formulation to give aldehyde 10 which is reduced with sodium borohydride to give alcohol 8. Additionally, 9 is converted to ester 11 by palladium (II) catalyzed coupling in the presence of carbon monoxide and methanol. Reduction of 11 with lithium aluminum hydride in tetrahydrofuran gives alcohol 8.

Scheme III

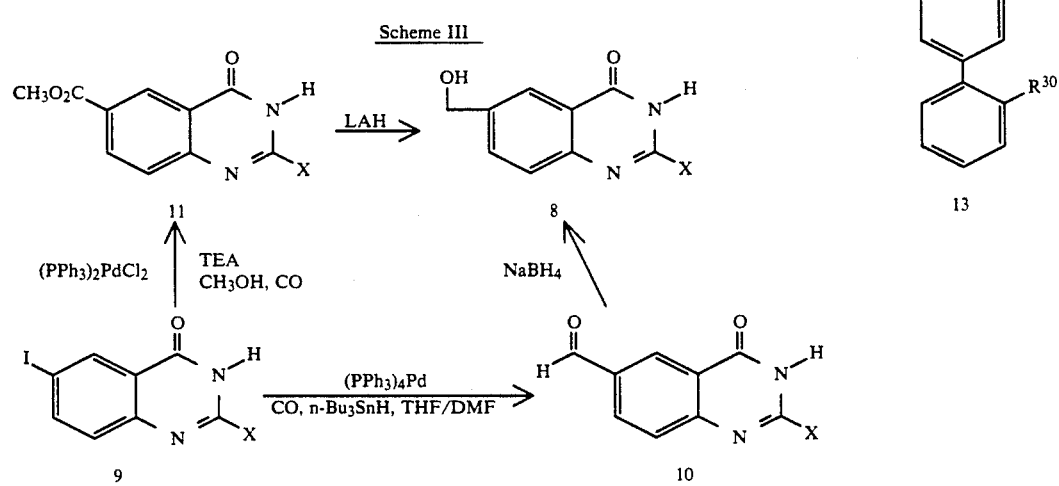

As described in EP 0497150, biphenyl 12 is attached to quinazolinone intermediate 8 by initially alkylating the quinazolinone with a para-substituted benzyl bromide and subsequently attaching a second phenyl moiety containing a trityl protected tetrazole or a cyano via a transition metal catalyzed coupling at the para position of the first phenyl ring.

Alternatively, as shown in Scheme IV, the quinazolinone intermediate 8 is coupled to biphenyl 12 where $R^{30}$ is a trityl protected tetrazole prepared by the methods of N.B. Mantlo, J. Med. Chem. 34, 2919–2922 (1991) or cyano prepared by methods outlined in D.J. Carini, J. Med. Chem. 34, 2525–2547 (1991) by dissolving in acetone or another suitable solvent such as N,N-dimethylformamide, N,N-dimethylacetamide, N-methylpyrrlidinone, ethanol, ethanol, t-butanol, tetrahydrofuran, dioxane or dimethylsulfoxide, in the presence of excess potassium carbonate or another suitable base such as sodium carbonate, cesium carbonate, sodium ethoxide, lithium methoxide, lithium diisopropylamide, lithium bis(trimethylsilyl)amide, sodium t-butoxide or potassium t-butoxide for 2–48 hours, at 20°–60° C.

4

The obtained alkylated quinazolinones 13 may be purified by chromatography or used as is in further transformations.

Scheme IV

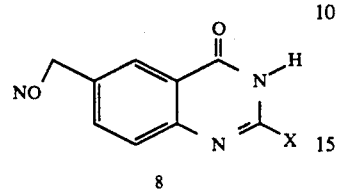

As shown in Scheme V, 2-lower alkyl substituted-6-(hydroxymethyl)-3-[[2'-[1-(triphenylmethyl)-1H-tetrazol-5-yl ]-[1,1'-biphenyl]-4-yl]methyl--4(3H)-quinazolinone 13 is reacted with methanesulfonyl chloride in the presence of triethylamine in tetrahydrofuran at −78° C., wherein X is hereinbefore defined to afford mesylate 14. The mesylate 14 and the heteroaryl alkoxides $R^6OM$, where $R^6$ is hereinbefore defined and M is Na or Li are dissolved in acetone or another suitable solvent such as N,N-dimethylformamide, N,N-dimethylacetamide, N-methylpyrrlidinone, methanol, ethanol, t-butanol, tetrahydrofuran, dioxane or dimethylsulfoxide, in the presence of excess potassium carbonate or other suitable base such as sodium carbonate, cesium carbonate, sodium hydride, potassium hydride, sodium methoxide, sodium ethoxide, lithium methoxide, sodium t-butoxide or potassium t-butoxide for 1-24 hours at 20°-60° C. to afford 15.

Reaction of 15 where $R^{30}$ is a trityl protected tetrazole with a refluxing aqueous acetone solution containing a catalytic amount of hydrochloric acid or other suitable acid such as sulfuric, tri-fluoroacetic or hydrogen chloride for 2-24 hours removes the trityl protecting group and affords 16. Additionally, heating 15 in tetrahydrofuran-methanol removes the trityl protecting group and affords 16. Reaction of 15 where $R^{30}$ is cyano with sodium azide in the presence of tri-n-butyltin chloride in refluxing xylene affords the desired tetrazole 16. Contemplated equivalents to tri-n-butyltin chloride include tri-(lower alkyl $C_1$-$C_4$) tin chlorides and bromides. Contemplated equivalents to sodium azide include potassium azide, cesium azide, calcium azide and lithium azide.

As outlined in Scheme VI, alcohol 13 is reacted with sodium hydride in tetrahydrofuran followed by the addition of 2-fluoropyridine to afford intermediate 17. Reaction of 17 where $R^{30}$ is a trityl protected tetrazole with a refluxing aqueous acetone solution containing a catalytic amount of hydrochloric acid or other suitable acid such as sulfuric, trifluoroacetic or hydrogen chloride for 2-24 hours removes the trityl protecting group and affords 18. Additionally, heating 17 in tetrahydrofuran-methanol removes the trityl protecting group and affords 18. Reaction of 17 where $R^{30}$ is cyano with sodium azide in the presence of tri-n-butyltin chloride in refluxing xylene affords the desired tetrazole 18. Contemplated equivalents to tri-n-butyltin chloride include tri-(lower alkyl $C_1$-$C_4$) tin chlorides and bromides. Contemplated equivalents to sodium azide include potassium azide, cesium azide, calcium azide and lithium azide.

-continued

Scheme V

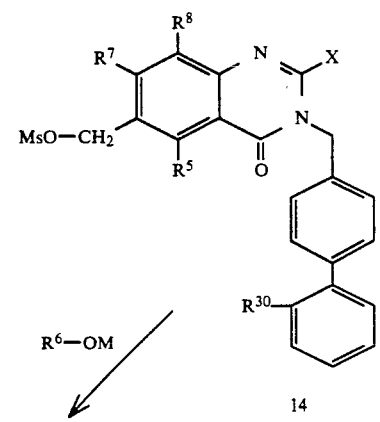

14

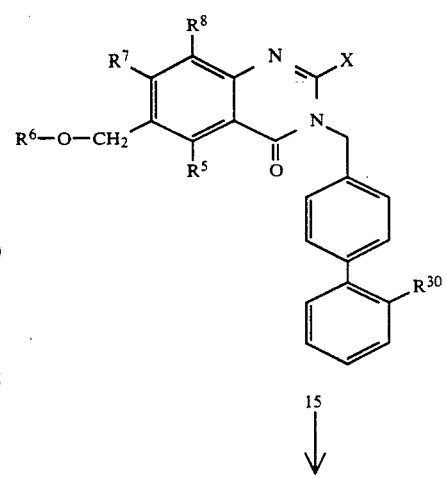

15

Scheme V

1080H

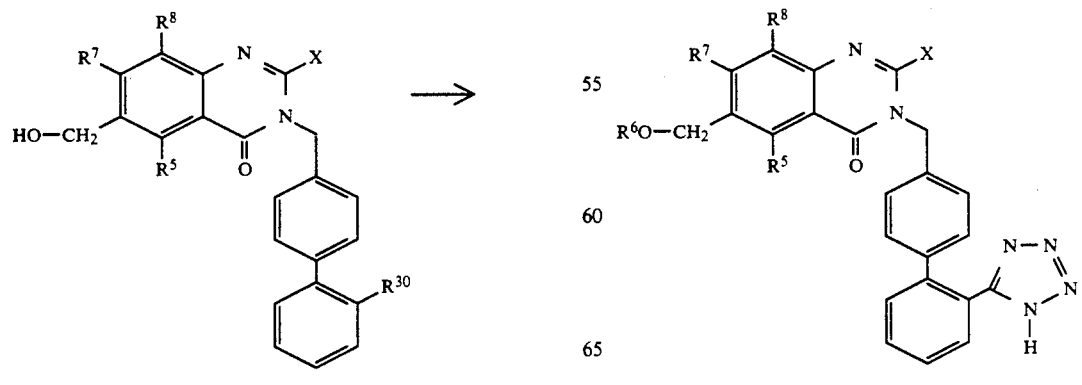

13

16

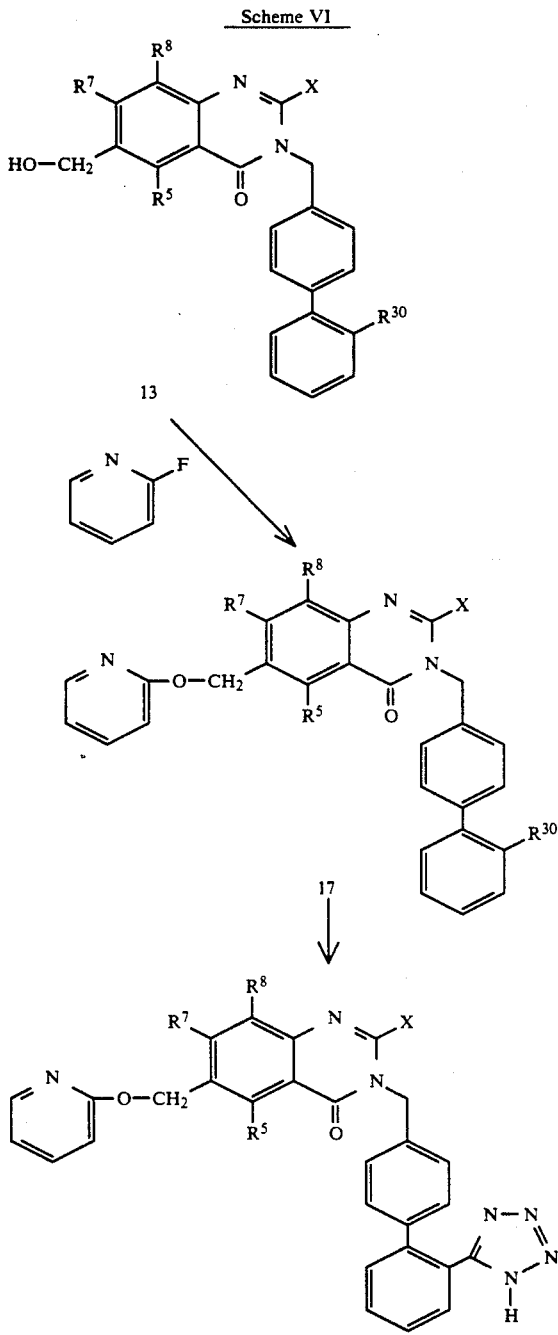

Reactions are performed in a solvent appropriate to the reagents and materials employed and suitable for the transformation being effected. It is understood by those skilled in the art of organic synthesis that the various functionalities present on the molecule must be consistent with the chemical transformations proposed. This will frequently necessitate judgement as to the other of synthetic steps, protecting groups, if required, and deprotection conditions. Substitutents on the starting materials may be incompatible with some of the reaction conditions. Such restrictions to the substituents which are compatible with the reaction conditions will be apparent to one skilled in the art.

Pharmaceutically suitable salts include both the metallic (inorganic) salts and organic salts; a list of which is given in *Remington's Pharmaceutical Sciences*, 17th Edition, pg. 1418 (1985). It is well known to one skilled in the art that an appropriate salt form is chosen based on physical and chemical stability, flowability, hygroscopicity and solubility. Preferred salts of this invention for the reasons cited above include potassium, sodium, calcium, magnesium and ammonium salts.

Some of the compounds of the hereinbefore described Schemes have centers of asymmetry. The compounds may, therefore, exist in at least two and often four stereoisomeric forms. The present invention encompasses all stereoisomers of the compounds whether free from other stereoisomers or admixed with other stereoisomers in any proportion and thus includes, for instance, racemic mixture of enantiomers as well as the diastereomeric mixture of isomers. The absolute configuration of any compound may be determined by conventional X-ray cyrstallography.

While the invention has been illustrated using the trityl protecting group on the tetrazole, it will be apparent to those skilled in the art that other nitrogen protecting groups may be utilized. Contemplated equivalent protecting groups include, benzyl, p-nitrobenzyl, propionitrile or any other protecting group suitable for protecting the tetrazole nitrogen. Additionally, it will be apparent to those skilled in the art that removal of the various nitrogen protecting groups, other than trityl, may require methods other than dilute acid.

The compounds of this invention and their preparation can be understood further by the following examples, but should not constitute a limitation thereof.

EXAMPLE 1

2-Butyl-6-(methyl-4(1H)-quinazolinone

Method A

To 20.0 g of 2-amino-5-methylbenzoic acid is added 60 ml of valeric anhydride. The mixture is heated at reflux for 18 hours and then concentrated under reduced pressure. The resulting brown solid residue is dissolved in a mixture of 200 ml of 30% of ammonium hydroxide solution and 300 ml of ethyl alcohol. This mixture is heated at reflux for 5 hours and then allowed to cool to room temperature. After cooling, the precipitate is collected by filtration. The cake is washed with ethanol and water, then dried under vacuum to give 8.92 g of the quinazolinone as a white solid.

CI MASS SPEC MH+ =217.

EXAMPLE 2

2-Butyl-6-iodo-4(1H)-quinazolinone

The method of Example 1 is used with 2-amino-5-iodobenzoic acid to prepare the desired product, m.p. 257°–258° C.

EXAMPLE 3

2-Butyl-6-(bromomethyl)-4)1H)-quinazolinone

To a suspension of 3.50 g of 6-methylquinazolinone in 100 ml of chloroform is added 3.39 g of N-bromosuccinimide and 0.25 g of benzoyl peroxide. The reaction mixture is heated at reflux for 18 hours and then filtered hot. A precipitate of 2.21 g of an inseparable mixture of the desired bromide and starting 6-methyl-quinazolinone is obtained and used in Example 4 without further purification.

EXAMPLE 4

2-Butyl-6-(hydroxymethyl)-4)1H)-quinazolinone

To a suspension of 2.0 g of impure 2-butyl-6-(bromomethyl)-4(1H)-quinazolinone (from Example 3) in 35 ml of dimethylsulfoxide and 20 ml of water is added 1.0 g of potassium carbonate. The reaction mixture is heated at reflux for 6 hours, resulting in a complete solution. Upon cooling slowly to room temperature a white precipitate forms and is collected by filtration. The filter cake is purified by flash chromatography on silica gel, eluting with 9:1 chloroform-methanol to give 0.67 g of the desired product as a white solid.

CI MASS SPEC 233(M+H).

EXAMPLE 5

2-Butyl-1,4-dihydro-4-oxo-6-quinazoline-carboxaldehyde

To a solution of 1.0 g of 2-butyl-6-iodo-4(1H)-quinazolinone and 0.355 g of tetrakis(triphenylphosphine)palladium in 15 ml of tetrahydrofuran and 5 ml of N,N-dimethylformamide, heated to 55° C. under an atmosphere of carbon monoxide is added a solution of 1.40 g of tri-n-butyltin hydride in 2.5 ml of toluene over 6 hours via a syringe pump. After the addition is complete the reaction is allowed to cool to room temperature, diluted with brine and extracted with chloroform. The combined organics are concentrated in vacuo and the resulting residue triturated with ether. The precipitate is collected by filtration and purified by flash chromatography on silica gel, eluting with 1:1 ethyl acetate-hexanes to give 0.35 g of the desired product, m.p. 242°-244° C.

EXAMPLE 6

Methyl 2-butyl-1,4-dihydro-4-oxo-6-quinazolinecarboxylate

To a solution of 1.00 g of 2-butyl-6-iodo-4(1H)-quinazolinone and 6.0 ml of triethylamine in 25 ml of methanol and 5 ml of N,N-dimethylformamide is added 0.275 g of bis-(triphenylphosphine)palladium (II) chloride. The reaction mixture is heated at reflux under an atmosphere of carbon monoxide for 16 hours, then allowed to cool and concentrated in vacuo. The residue is purified by flash chromatography on silica gel, eluting with 1:1 ethyl acetate-hexanes to give 0.389 g of the desired product as a white solid.

CI MASS SPEC 261(MH$^{30}$).

EXAMPLE 7

2-Butyl-6-(hydroxymethyl)-4-(1H)-quinazolinone

To a suspension of 0.013 g of lithium aluminum hydride in 5.0 ml of tetrahydrofuran is added 0.100 g of methyl 2-butyl-1,4-dihydro-4-oxo-6-quinazolinecarboxylate followed by stirring at room temperature for 5 hours. An additional 20 mg of lithium aluminum hydride is added and stirring continued for 18 hours. An additional 20 mg of lithium aluminum hydride is added and stirring continued for an additional 8 hours. The reaction mixture is poured into 75 ml of water and extracted with ethyl acetate. The extract is evaporated in vauco to a residue which is stirred with acetone and filtered to give 0.040 g of the desired product as a white solid.

CI MASS SPEC 233(M+H)

EXAMPLE 8

2-Butyl-6-(hydroxymethyl)-3-[[2'-[1-(triphenylmethyl)-1H)-tetrazol-5-yl][1,1'-biphenyl]-4-yl]methyl]-4(3H)-quinazolinone A suspension of 0.198 g of 2-butyl-6-hydroxymethyl-4(1H)-quinazolinone, 0.477 g of 5-[4'-(bromomethyl)[1,1'-biphenyl]-2-yl]-1-(triphenylmethyl)-1H-tetrazole and 0.500 g of potassium carbonate in 15.0 ml of acetone is heated at reflux for 18 hours. The reaction mixture is allowed to cool to room temperature and evaporated in vacuo. The residue is diluted with water and extracted with chloroform. The organic layer is washed with brine and evaporated in vacuo to a residue which is purified by chromatography using silica gel preparative plates by elution with 1:1 ethyl acetate-hexanes to give 0.145 g of the desired product as a solid.

FAB MASS SPEC 709(M+H)

EXAMPLE 9

2-Butyl-6-[[(methylsulfonyl)oxy]methyl]-3-[[2'-[1-(triphenylmethyl)-1H-tetrazol-5-yl][1,1'-biphenyl]-4-yl]methyl]-4(3H)-quinazolinone A solution of 0.250 g of 2-butyl-6-(hydroxymethyl)-3-[[2'-[1-(triphenylmethyl)-1H-tetrazol-5-yl]-[1,1'-biphenyl]-4-yl]methyl-4(3H)-quinazolinone and 0.246 ml of triethylamine in 5.0 ml of tetrahydrofuran is cooled to −78° C. and while stirring 0.137 ml of methanesulfonyl chloride is added. The reaction mixture is allowed to warm to room temperature and stirred for 18 hours. The reaction mixture is portioned between water and chloroform. The organic layer is separated and washed with 5% HCl and saturated sodium bicarbonate, dried with magnesium sulfate, filtered and evaporated to afford 0.278 g of the desired product.

FAB MASS SPEC 787(M+H)

EXAMPLE 10

2-Butyl-6-[(2-pyridinyloxy)methyl]-3-[[2'-[1-(triphenylmethyl)-1H-tetrazol-5-yl][1,1'-biphenyl]-4-yl]methyl]-4(3H)-quinazolinone A mixture of 0.278 g of 2-butyl-6-[[methylsulfonyl)oxy]methyl]-3-[[2'-[1-(triphenyl methyl)-1H-tetrazol-5-yl][1,1'-biphenyl]-4-yl]methyl]-4(3H)-quinazolinone 0.067 g of 2-hydroxypyridine and 0.098 g of potassium carbonate in 5 ml of acetone is heated to reflux for 18 hours. The reaction mixture is cooled to room temperature, filtered and the filtrate concentrated. The concentrate is columned on silica gel using ethyl acetate and ethyl acetate-hexanes to afford the desired product.

FAB MASS SPEC 786(M+H)

EXAMPLE 11

2-Butyl-6-[(2-pyridinyloxy)methyl]-3-[[2'-[1-(triphenylmethyl)-1H-tetrazol-5-yl][1,1'-biphenyl]-4-yl]methyl]-4-(3H)-quinazolinone A solution of 0.200 g of 2-butyl-6-(hydroxymethyl)-3-[[2'-[1-(triphenylmethyl)-1H-tetrazo-5-yl]-[1,1'-biphenyl]-4-yl]methyl-4(3H)-quinazolinone in 2.0 ml of tetrahydrofuran is treated with 0.023 g of 60% sodium hydride followed by the addition of 0.137 g of 2-fluoropyridine. The reaction mixture is stirred at room temperature for 10 hours. An additional 0.012 g of sodium hydride and 0.137 g of 2-fluoropyridine is added followed by stirring at room temperature for 18 hours. The reaction mixture is quenched with aqueous ammonium chloride solution and extracted with chloroform. The organic layer is dried with magnesium sulfate and evaporated to a residue which is purified by chromatography on silica gel using 1:1 ethyl acetate-hexanes to afford 0.157 g of the desired product.

FAB MASS SPEC 786(M+H)

EXAMPLE 12

2-Butyl-6-[(2-pyridinyloxy)methyl]-3-[[2'-(1H-tetrazol-5-yl)[1,1'-biphenyl ]-4-yl]methyl]-4(3H)-quinazolinone monohydrochloride A mixture of 0.147 g of 2-butyl-6-[(2-pyridinyloxy)methyl]-3-[[2'-[1-(triphenyl methyl)-1H-tetrazol-5-yl][1,1'-biphenyl]-4-yl]methyl-4(3H)-quinazoli none, 5.0 ml of ether and 3.0 ml of 3.0 M HCl in ethyl acetate is stirred at room temperature for 1 hour. The reaction mixture is diluted with 5 ml of ether, filtered and the solid dried to afford 0.100 g of the desired product.

FAB MASS SPEC 544(M+H)

Utilizing the methodology described herein, the following compounds are also obtained:

2-Butyl-6-[(2-thienyloxy)methyl]-3-[[2'-[1-(tri-phenylmethyl)-1H-tetrazol-5-yl ][1,1'-biphenyl]-4-yl]methyl]-4(3H)-quinazolinone 2-Butyl-6-[(2-furanyloxy)methyl]-3-[[2'-[1-(tri-phenylmethyl)-1H-tetrazol-5-yl ][1,1'-biphenyl]-4-yl]methyl]-4(3H)-quinazolinone 2-Butyl-6-[(3-thienyloxy)methyl]-3-[[2'-[1-(tri-phenylmethyl)-1H-tetrazol-5-yl ][1,1'-biphenyl]-4-yl]methyl]-4(3H)-quinazolinone 2-Butyl-6-[(3-furanyloxy)methyl]-3-[[2'-[1-(tri-phenylmethyl)-1H-tetrazol-5-yl ][1,1'-biphenyl]-4-yl]methyl]-4(3H)-quinazolinone 2-Butyl-6-[(2-thienyloxy)methyl]-3-[[2'-(1H-tetrazol-5-yl) [1,1'-biphenyl]-4-yl]methyl]-4(3H)-quinazolinone monohydrochloride 2-Butyl-6-[(3-thienyloxy)methyl]-3-[[2'-(1H-tetrazol-5-yl) [1,1'-biphenyl]-4-yl]methyl]-4(3H)-quinazolinone 2-Butyl-6-[(3-furanyloxy)methyl]-3-[[2'-(1H-tetrazol-5-yl) [1,1'-biphenyl]-4-yl]methyl]-4(3H)-quinazolinone monohydrochloride 2-Butyl-6-[(2-furanyloxy)methyl]-3-[[2'-(1H-tetrazol-5-yl) [1,1'-biphenyl]-4-yl]methyl]-4(3H)-quinazolinone monohydrochloride

Angiotensin II Antagonists In Vitro Tests Materials and Methods

Beef adrenals are obtained from a local slaughter house (Maxwell-Cohen). [$^{125}$I](Sar$^1$,Ile$^8$)AngII, S.A. 2200 Ci/mmole, is purchased from Dupont (NEN ®, Boston, Mass.). All unlabeled AngII analogs, Dimethylsulfoxide (DMSO), nucleotides, bovine serum albumin (BSA) are purchased from Sigma Chemical Co., St. Louis, MO U.S.A.

Preparation of Membranes

Approximately sixteen (16) to twenty (20) beef adrenal glands are processed as follows: fresh adrenal glands received on crushed ice are cleaned of fatty tissues and the tough membranes encapsulating the glands are removed and discarded. The brownish tissue forming the adrenal cortex is scraped off and finely minced with scissors before homogenization. Care is taken to avoid contamination with medullary tissue during dissection. The scraped cortices are suspended in twenty volumes of an ice-cold buffer medium consisting of 10 mM Tris.HCl (pH 7.4 at 22° C.) and containing 1.0 mM EDTA and 0.2M sucrose. Unless otherwise indicated, all subsequent operations are done at 4° C. The tissue is homogenized in a glass homogenizer with a motor driven teflon pestle with a clearance of 1.0 mm. The homogenate is centrifuged first at low speed (3,000×g) for 10 min. The resulting pellet is discarded and the supernatant fluid recentrifuged at 10,000 x g for 15 minutes to give a P$_2$ pellet. This P$_2$ pellet is discarded and the liquid phase is carefully decanted off in clean centrifuge tubes and recentrifuged at high speed (100,000 ×g) for 60 min. The translucent final pellet is harvested and combined in a small volume (20–50.0ml) of 50.0 mM Tris.HCl buffer, pH 7.2. A 100 ul aliquot is withdrawn and the protein content of the preparation is determined by the Lowry's method (Lowry, O.H., Rosebrough, N.F., Farr, A.L. and Randall, R.J., Protein measurement with Folin phenol reagent. J. Biol. Chem., 48, 265–275, 1951). The pelleted membrane is reconstituted in 50.0 mM Tris.HCl buffer containing 0.1 mM of phenylmethylsulfonyl fluoride (PMSF) to give approximately a protein concentration of 2.5 mg per ml of tissue suspension. The membrane preparation is finally aliquoted in 1.0 ml volumes and stored at −70° C. until use in the binding assays.

Receptor Binding Assay

Binding of [$^{125}$I](Sar$^1$, Ile$^8$)AngII

The binding of [$^{125}$I](Sar$^1$, Ile$^8$)AngII to microsomal membranes is initiated by the addition of reconstituted membranes (1:10 vols.) in freshly made 50.0 mM Tris.HCl buffer, pH 7.4 containing 0.25% heat inactivated bovine serum albumin (BSA): 80 ul membrane protein (10 to 20 ug/assay) to wells already containing 100 ul of incubation buffer (as described above) and 20 ul [$^{125}$I](Sar$^1$, Ile$^8$)AngII (Specific Activity, 2200 Ci/mmole). Non-specific binding is measured in the presence of 1.0 uM unlabeled (Sar$^1$, Ile$^8$)AngII, added in 20 ul volume. Specific binding for [$^{125}$I](Sar$^1$, Ile$^8$) AngII is greater than 90%. In competition studies, experimental compounds are diluted in dimethylsulfoxide (DMSO) and added in 20 ul to wells before the introduction of tissue membranes. This concentration of DMSO is found to have no negative effects on the binding of [$^{125}$I](Sar$^1$, Ile$^8$)AngII to the membranes. Assays are performed in triplicate. The wells are left undisturbed for 60 min. at room temperature. Following incubation, all wells are harvested at once with a Brandel ® Harvester especially designed for a 96 well plate (Brandel ® Biomedical Research & Development Labs. Inc., Gaithersburg, MD, U.S.A.). The filter discs are washed with 10×1.0 ml of cold 0.9% NaCl to remove unbound ligand. Presoaking the filter sheet in 0.1% polyethyleneimine in normal saline (PEI/Saline) greatly reduces the radioactivty retained by the filter blanks. This method is routinely used. The filters are removed from the filter grid and counted in a Parkard ® Cobar Gamma Conder for 1 min. (Packard Instrument Co., Downers Grove, Ill, U.S.A.). The binding data are analyzed by the non-linear interactive "LUNDON-1" program (LUNDON SOFTWARE Inc., Cleveland, OH U.S.A.). Compounds that displace 50% of the labelled angiotensin II at the screening dose of 50 μM are considered active compounds and are then evaluated in concentration-response experiments to determine their IC$_{50}$ values. The results are shown in Table III.

As can be seen from Table III, the compounds demonstrate excellent Angiotensin II Receptor Binding activity.

The enzyme renin acts on a blood plasma α$_2$-globulin, angiotensinogen, top produce angiotensin I, which is then converted by angiotensin converting enzyme to AII. The substance AII is a powerful vasopressor agent which is implicated as a causative agent for producing high blood pressure in mammals. Therefore, compounds which inhibit the action of the hormone angiotensin II (AII) are useful in alleviating angiotensin induced hypertension.

TABLE III

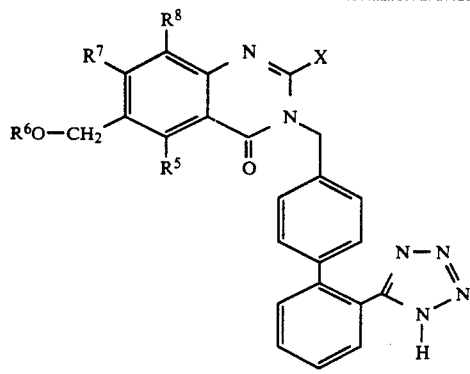

| Ex. No. | $R^5$ | $R^6$ | $R^7$ | $R^8$ | X | Angiotensin II Receptor Binding IC$_{50}$ (M) |
|---|---|---|---|---|---|---|
| 12 | H | 2-pyridyl | H | H | —(CH$_2$)$_3$CH$_3$ | $13 \times 10^{-8}$ |

The compounds of this invention inhibit the action of AII. By administering a compound of this invention to a rat, and then challenging with angiotensin II, a blockage of the vasopressor response is realized. The results of this test on representative compounds of this invention are shown in Table V.

AII Challenge

Conscious Male Okamoto-Aoki SHR, 16-20 weeks old, weighing approximately 330 g are purchased from Charles River Labs (Wilmington, MA). Conscious rats are restrained in a supine position with elastic tape. The area at the base of the tail is locally anesthetized by subcutaneous infiltration with 2% procaine. The central caudal artery and vein are isolated, and a cannula made of polyethylene (PE) 10-20 tubing (fused together by heat) is passed into the lower abdominal aorta and vena cava, respectively. The cannula is secured, heparinized (1,000 I.U./ml), sealed and the wound is closed. The animals are placed in plastic restraining cages in an upright position. The cannula is attached to a Statham P23Db pressure transducer, and pulsatile blood pressure is recorded to 10-15 minutes with a Gould Brush recorder. (Chan et al., (Drug Development Res., 18:75-94, 1989).

Angiotensin II (human sequence, Sigma Chem. Co., St. Louis, MO) of 0.05 and 0.1 ug/kg i.v. is injected into all rats (predosing repsonse). Then a test compound, vehicle or a known angiotensin II antagonist is administered i.v., i.p. or orally to each set of rats. The two doses of angiotensin II are given to each rat again at 30, 60, 90, 120, 180, 240 and 300 minutes post dosing the compound or vehicle. The vasopressor response of angiotensin II is measured for the increase in systolic blood pressure in mmHg. The percentage of antagonism or blockade of the vasopressor response of angiotensin II by a compound is calculated using the vasopressor response (increase in systolic blood pressure) of angiotensin II of each rat predosing the compound as 100%. A compound is considered active if at 30 mg/kg i.v. it antagonized at least 50% of the response.

TABLE IV

| Ex. No. | Dose (mg/kg) | AII Dose mcg/kg IV | Min Post Dose | Control Before AII | Response After AII | Change | Average Change | % Inhibition |
|---|---|---|---|---|---|---|---|---|
|  |  | 0.05 | 0 | 185 | 215 | 30 | 32.5 |  |
|  |  |  |  | 170 | 205 | 35 |  |  |
|  |  | 0.1 |  | 175 | 215 | 40 | 42.5 |  |
|  |  |  |  | 175 | 220 | 45 |  |  |
| 12 | 5 IV | 0.05 | 30 | 185 | 195 | 10 | 12.5 | 62 |
|  |  |  |  | 180 | 195 | 15 |  |  |
|  |  | 0.1 |  | 185 | 195 | 10 | 15 | 65 |
|  |  |  |  | 175 | 195 | 20 |  |  |
|  |  | 0.05 | 60 | 175 | 175 | 0 | 2.5 | 92 |
|  |  |  |  | 175 | 180 | 5 |  |  |
|  |  | 0.1 |  | 170 | 185 | 15 | 12.5 | 71 |
|  |  |  |  | 175 | 185 | 10 |  |  |
|  |  | 0.05 | 90 | 160 | 170 | 10 | 10 | 69 |
|  |  |  |  | 165 | 175 | 10 |  |  |
|  |  | 0.1 |  | 160 | 170 | 10 | 10 | 76 |
|  |  |  |  | 170 | 180 | 10 |  |  |
|  |  | 0.05 | 120 | 165 | 175 | 10 | 7.5 | 77 |
|  |  |  |  | 165 | 170 | 5 |  |  |
|  |  | 0.1 |  | 165 | 185 | 20 | 15 | 65 |
|  |  |  |  | 165 | 175 | 10 |  |  |
|  |  | 0.05 | 180 | 165 | 172 | 7 | 11 | 66 |
|  |  |  |  | 155 | 170 | 15 |  |  |
|  |  | 0.1 |  | 160 | 180 | 20 | 21 | 51 |
|  |  |  |  | 160 | 182 | 22 |  |  |
|  |  | 0.05 | 0 | 180 | 225 | 45 | 40 |  |
|  |  |  |  | 200 | 235 | 35 |  |  |
|  |  | 0.1 |  | 185 | 228 | 43 | 41.5 |  |
|  |  |  |  | 200 | 240 | 40 |  |  |
| 12 | 10 P.O. | 0.05 | 30 | 185 | 210 | 25 | 17.5 | 56 |
|  |  |  |  | 200 | 210 | 10 |  |  |
|  |  | 0.1 |  | 185 | 220 | 35 | 27.5 | 34 |
|  |  |  |  | 200 | 220 | 20 |  |  |
|  |  | 0.05 | 60 | 195 | 220 | 25 | 22.5 | 44 |
|  |  |  |  | 185 | 205 | 20 |  |  |

TABLE IV-continued

% INHIBITION (ANGIOTENSIN BLOCKAGE) OF ANGIOTENSIN II (AII) VASOPRESSOR RESPONSE

| Ex. No. | Dose (mg/kg) | AII Dose mcg/kg IV | Min Post Dose | Control Before AII | Response After AII | Change | Average Change | % Inhibition |
|---|---|---|---|---|---|---|---|---|
| | | 0.1 | | 185 | 220 | 35 | 35 | 16 |
| | | | | 185 | 220 | 35 | | |
| | | 0.05 | 90 | 190 | 220 | 30 | 16.5 | 59 |
| | | | | 195 | 198 | 3 | | |
| | | 0.1 | | 190 | 220 | 30 | 30 | 28 |
| | | | | 190 | 220 | 30 | | |
| | | 0.05 | 120 | 210 | 230 | 20 | 12.5 | 69 |
| | | | | 210 | 215 | 5 | | |
| | | 0.1 | | 205 | 235 | 30 | 20 | 52 |
| | | | | 205 | 215 | 10 | | |
| | | 0.05 | 180 | 185 | 210 | 25 | 20 | 50 |
| | | | | 185 | 200 | 15 | | |
| | | 0.1 | | 190 | 225 | 35 | 25 | 40 |
| | | | | 195 | 210 | 15 | | |

When the compounds are employed for the above utility, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in sustained release form. For most large mammals the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

What is claimed is:

1. A quinazolinone compound having the formula:

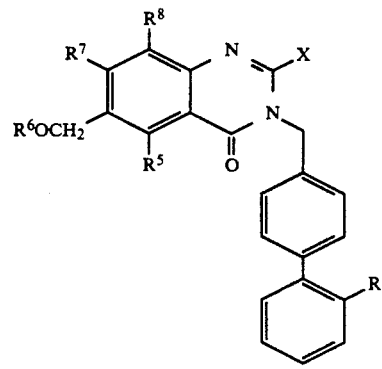

wherein
R is

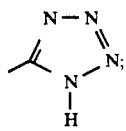

X is straight or branched alkyl of 3 to 5 carbon atoms;
R⁵, R⁷ and R⁸ are H;
R⁶ is

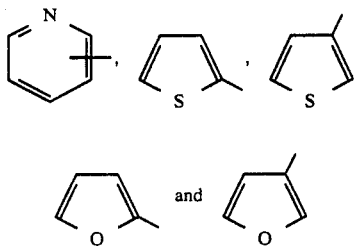

or the pharmaceutically acceptable salts thereof.

2. The compound according to claim 1 wherein X is a straight chain alkyl of 4 carbon atoms.

3. The compound according to claim 1 wherein X is a straight chain alkyl of 3 or 4 carbon atoms; R⁶ is

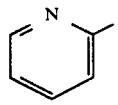

4. A quinazolinone compound having the formula:

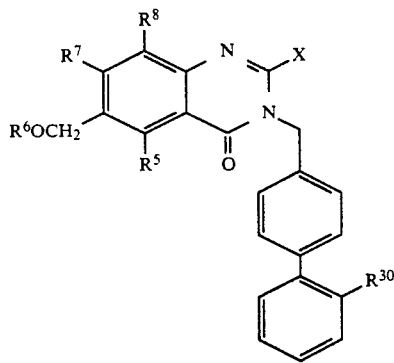

wherein
X is a straight or branched alkyl of 3 to 5 carbon atoms;
R³⁰ is

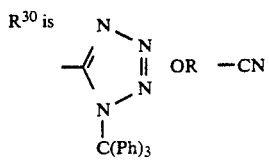

R⁵, R⁷ and R⁸ are H;
R⁶ is

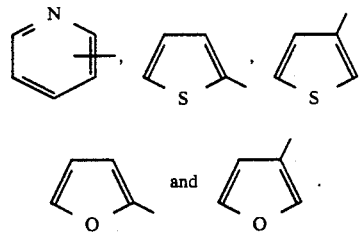

5. The compound according to claim 4 wherein X is a straight chain alkyl of 3 or 4 carbon atoms; R⁶ is

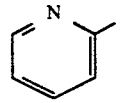

6. The compound according to claim 1 2-Butyl-6-[(2-pyridinyloxy)methyl]-3-[[2'-(1H-tetrazol-5-yl)[1,1'-biphenyl]-4-yl]methyl]-4(3H)-quinazolinone monohydrochloride.

7. The compound according to claim 1 2-Butyl-6-[(2-thienyloxy)methyl]-3-[[2'-(1H-tetrazol-5-yl)[1,1'-biphenyl]-4-yl]methyl]-4(3H)-quinazolinone monohydrochloride.

8. The compound according to claim 1 2-Butyl-6-[(2-thienyloxy)methyl]-3-[[2'-(1H-tetrazol-5-yl)[1,1'-biphenyl]-4-yl]methyl]-4(3H)-quinazolinone.

9. The compound according to claim 1 2-Butyl-6-[(3-furanyloxy)methyl]-3-[[2'-(1H-tetrazol-5-yl)[1,1'-biphenyl]-4-yl]methyl]-4(3H)-quinazolinone monohydrochloride.

10. The compound according to claim 1 2-Butyl-6-[(2-furanyloxy)methyl]-3-[[2'-(1H-tetrazol-5-yl)[1,1'-biphenyl]-4-yl]methyl]-4(3H)-quinazolinone monohydrochloride.

11. The compound according to claim 4 2-Butyl-6-[(2-furanyloxy)methyl]-3-[[2'-[1-(triphenylmethyl)-1H-tetrazol-5-yl][1,1'-biphenyl]-4-yl]methyl]-4(3H)-quinazolinone.

12. The compound according to claim 4 2-Butyl-6-[(2-thienyloxy)methyl]-3-[[2'-[1-(triphenylmethyl)-1H-tetrazol-5-yl][1,1'-biphenyl]-4-yl]methyl]-4(3H)-quinazolinone.

13. The compound according to claim 4 2-Butyl-6-[(2-furanyloxy)methyl]-3-[[2'-[1-(triphenylmethyl)-1H-tetrazol-5-yl][1,1'-biphenyl]-4-yl]methyl]-4(3H)-quinazolinone.

14. The compound according to claim 4 2-Butyl-6-[(3-thienyloxy)methyl]-3-[[2'-[1-(triphenylmethyl)-1H-tetrazol-5-yl][1,1'-biphenyl]-4-yl]methyl]-4(3H)-quinazolinone.

15. The compound according to claim 4 2-Butyl-6-[(3-furanyloxy)methyl]-3-[[2'-[1-(triphenylmethyl)-1H-tetrazol-5-yl][1,1'-biphenyl]-4-yl]methyl]-4(3H)-quinazolinone.

16. The compound 2-Butyl-6-[[(methylsulfonyl)oxy]methyl]-3-[[2'-[1-(triphenylmethyl)-1H-tetrazol-5-yl][1,1'-biphenyl]-4-yl]methyl]-4(3H)-quinazolinone.

17. A pharmaceutical composition useful for treating angiotensin induced hypertension or congestive heart failure in a mammal comprising a suitable pharmaceutical carrier and an effective amount of a compound of claim 1.

18. A method of treating angiotensin induced hypertension in a mammal comprising administering a compound of claim 1 to said mammal an amount effective to lower angiotensin induced hypertension.

19. A method of treating congestive heart failure in a mammal comprising administering a compound of claim 1 to said mammal in an amount effective to treat congestive heart failure.

* * * * *